(12) United States Patent
Toth et al.

(10) Patent No.: US 6,829,323 B2
(45) Date of Patent: Dec. 7, 2004

(54) METHOD AND SYSTEM FOR LOW DOSE IMAGE SIMULATION FOR IMAGING SYSTEMS

(75) Inventors: Thomas Louis Toth, Brookfield, WI (US); Jiang Hsieh, Brookfield, WI (US); Jianying Li, New Berlin, WI (US); Scott Matt McOlash, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 177 days.

(21) Appl. No.: 10/064,586

(22) Filed: Jul. 29, 2002

(65) Prior Publication Data

US 2004/0017880 A1 Jan. 29, 2004

(51) Int. Cl.[7] .............................................. A61B 6/03
(52) U.S. Cl. ........................................ 378/4; 378/901
(58) Field of Search ........................... 378/4, 8, 15, 19, 378/901

(56) References Cited

U.S. PATENT DOCUMENTS 6,272,200 B1 * 8/2001 Pan et al. ...................... 378/15

OTHER PUBLICATIONS

European Search Report 15CT124608/9477 dated Jan. 23, 2004.

H. Greess, A. Homayr, H. Wolf, U. Baum, M. Lell, B. Bowing, W. Kalender, W. Bautz; "Dose reduction in CT examination of children by an attenuation–based on–line modulation of tube current (CARE Dose);" Eur. Radiol; (2002); pp. 1571–1576.

P. Lahorte, S Vandenberghe, K. Van Laere, K. Audenaert, I Lemahieu, and R. A. Dierckx; "Rapid Communication—Assessing the Performance of SPM Analyses of Spect Neuroactivation Studies;" NeuroImage 12, (2000); pp. 757–764.

Frush et al. "Computer–simulated radiation dose reduction for pediatric abdominal helical CT;" 4th International Pediatric Radiology Meeting; (May 28, 2001); p. 1–2.

A. Barnes, D. Dal, D. Montaldi, J. Patterson, and D. Wyper; "Image quality versus statistical power;" Nuclear Medicine Communications, 1997, 18, pp. 1155–1160.

* cited by examiner

*Primary Examiner*—David V Bruce
(74) *Attorney, Agent, or Firm*—Cantor Colburn LLP

(57) ABSTRACT

A method for generating a simulated patient image is disclosed. In an exemplary embodiment, the method includes obtaining image data from an actual patient image and generating simulated noise data. The image data is then combined with the simulated noise data to create the simulated patient image. In one aspect, scan data from the actual patient image is combined with the generated simulated noise data to create pre-image data, and the pre-image data is then reconstructed to create simulated image data. In another aspect, a set of individual noise pattern images for each a plurality of phantom objects is created. At least one of the individual noise pattern images is selected for combination with the actual patient image. The at least one selected individual noise pattern image is then combined with the actual patient image, thereby creating the simulated patient image.

44 Claims, 3 Drawing Sheets

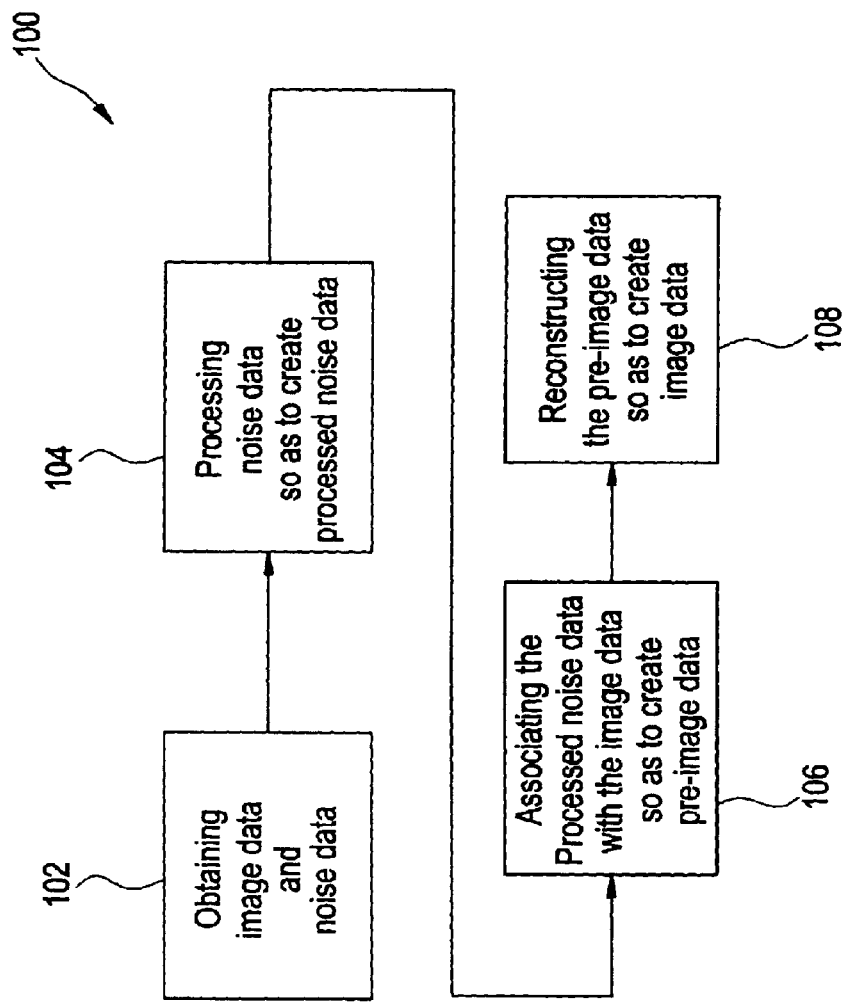

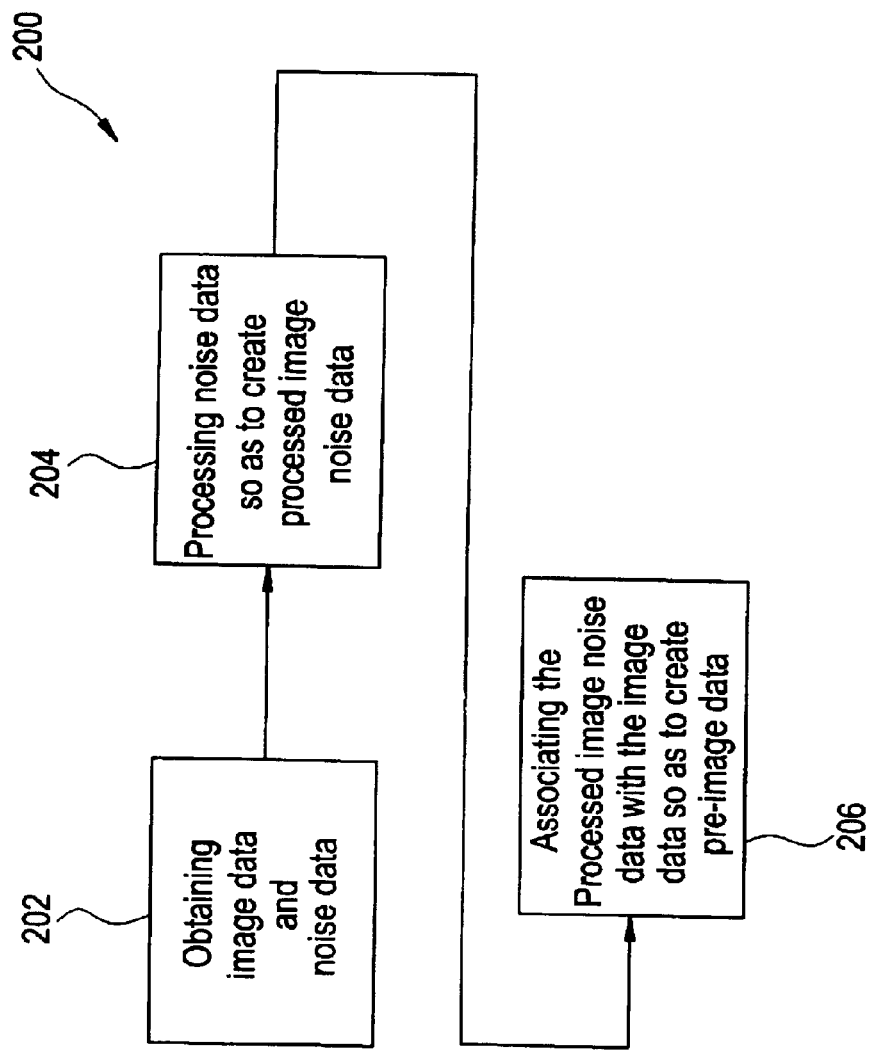

METHOD AND SYSTEM FOR LOW DOSE IMAGE SIMULATION FOR IMAGING SYSTEMS

BACKGROUND OF INVENTION

The present disclosure relates generally imaging systems and, more particularly, to improving the dose efficiency for an imaging system through a method and system for image simulation at lower doses.

In at least one known computed tomography (CT) imaging system configuration, an x-ray source projects a fan-shaped beam which is collimated to lie within an X-Y plane of a Cartesian coordinate system, wherein the X-Y plane is generally referred to as an "imaging plane". An array of radiation detectors, wherein each radiation detector includes a detector element, are within the CT system so as to receive this fan-shaped beam. An object, such as a patient, is disposed within the imaging plane so as to be subjected to the x-ray beam wherein the x-ray beam passes through the object. As the x-ray beam passes through the object being imaged, the x-ray beam becomes attenuated before impinging upon the array of radiation detectors. The intensity of the attenuated beam radiation received at the detector array is responsive to the attenuation of the x-ray beam by the object, wherein each detector element produces a separate electrical signal responsive to the beam attenuation at the detector element location. These electrical signals are referred to as x-ray attenuation measurements.

In addition, the x-ray source and the detector array may be rotated, with a gantry within the imaging plane, around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and the detector array. In an axial scan, the projection data is processed so as to construct an image that corresponds to a two-dimensional slice taken through the object.

One method for reconstructing an image from a set of projection data is referred to as the "filtered back-projection technique". This process converts the attenuation measurements from a scan into discrete integers, ranging from −1024 to +3071, called "CT numbers" or "Hounsfield Units" (HU). These HU's are used to control the brightness of a corresponding pixel on a cathode ray tube or a computer screen display in a manner responsive to the attenuation measurements. For example, an attenuation measurement for air may convert into an integer value of −1000 HU's (corresponding to a dark pixel) and an attenuation measurement for very dense bone matter may convert into an integer value of +2000 (corresponding to a bright pixel), whereas an attenuation measurement for water may convert into an integer value of 0 HU's (corresponding to a gray pixel). This integer conversion, or "scoring" allows a physician or a technician to determine the density of matter based on the intensity of the computer display.

Although imaging systems, such as the CT imaging system, are excellent diagnostic and evaluation tools, each time a scan is performed the patient being scanned is exposed to radiation. In fact, CT scans account for only about 2% to 3% of medical examinations using imaging systems. However, they account for 30% to 50% of the population radiation dose from these procedures. Given that exposure to greater than average amounts of radiation is known to cause health problems, there is concern within the medical community that a patient may be over exposed. As such, there is a continuing but increasingly limited effort to reduce the amount of patient exposure by improving the imaging dose efficiency. This effort includes researchers investigating and determining the minimum dose required to obtain the image quality necessary to make an accurate and confident diagnosis for a given clinical application. As patient dose is decreased, the image noise is increased, making lesions more difficult to detect.

In order obtain the data needed to find the minimum dose necessary to make a confident diagnosis a reference object, such as a patient, must undergo multiple scans at different dose levels. Unfortunately, this may be considered unethical, inappropriate and potentially detrimental to the patient(s) being scanned for these purposes. Accordingly, it is desirable to be able to determine minimum dose information without the need for exposing a patient to excessive radiation doses.

SUMMARY OF INVENTION

The above discussed and other drawbacks and deficiencies are overcome or alleviated by a method for generating a simulated patient image. In an exemplary embodiment, the method includes obtaining image data from an actual patient image and generating simulated noise data. The image data is then combined with the simulated noise data to create the simulated patient image. In one embodiment, scan data from the actual patient image is combined with the generated simulated noise data to create pre-image data, and the pre-image data is then reconstructed to create simulated image data. In another embodiment, a set of individual noise pattern images for each a plurality of phantom objects is created. At least one of the individual noise pattern images is selected for combination with the actual patient image. The at least one selected individual noise pattern image is then combined with the actual patient image, thereby creating the simulated patient image.

In another aspect, a method for generating a simulated computer tomography (CT) patient image includes obtaining image data from an actual CT patient image taken at a first radiation dose, and generating simulated noise data. The image data is then combined with the simulated noise data to create the simulated patient image, wherein the simulated image simulates the actual CT patient image taken at a second, reduced radiation dose with respect to the first radiation dose.

In another aspect, an imaging system includes a gantry having an x-ray source and a radiation detector array, wherein the gantry defines a patient cavity and wherein the x-ray source and the radiation detector array are rotatingly associated with the gantry so as to be separated by the patient cavity. A patient support structure is movingly associated with the gantry so as to allow communication with the patient cavity. In addition, a processing device is used for obtaining image data from an actual patient image. The imaging system further includes means for generating simulated noise data, and means for combining the image data with the simulated noise data to create a simulated patient image.

In still another aspect, a storage medium includes a machine readable computer program code for generating a simulated patient image, and instructions for causing a computer to implement a method. The method includes obtaining image data from an actual patient image, generating simulated noise data and combining the image data with the simulated noise data to create the simulated patient image.

In still another aspect, a computer data signal includes code configured to cause a processor to implement a method for generating a simulated patient image. The method includes obtaining image data from an actual patient image, generating simulated noise data and combining the image data with the simulated noise data to create the simulated patient image.

The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures:

FIG. 3 is a block diagram describing a first embodiment of a method for simulating patient images generated by an imaging system; and FIG. 4 is a block diagram describing a second embodiment of a method for simulating patient images generated by an imaging system.

DETAILED DESCRIPTION

Figure 1:
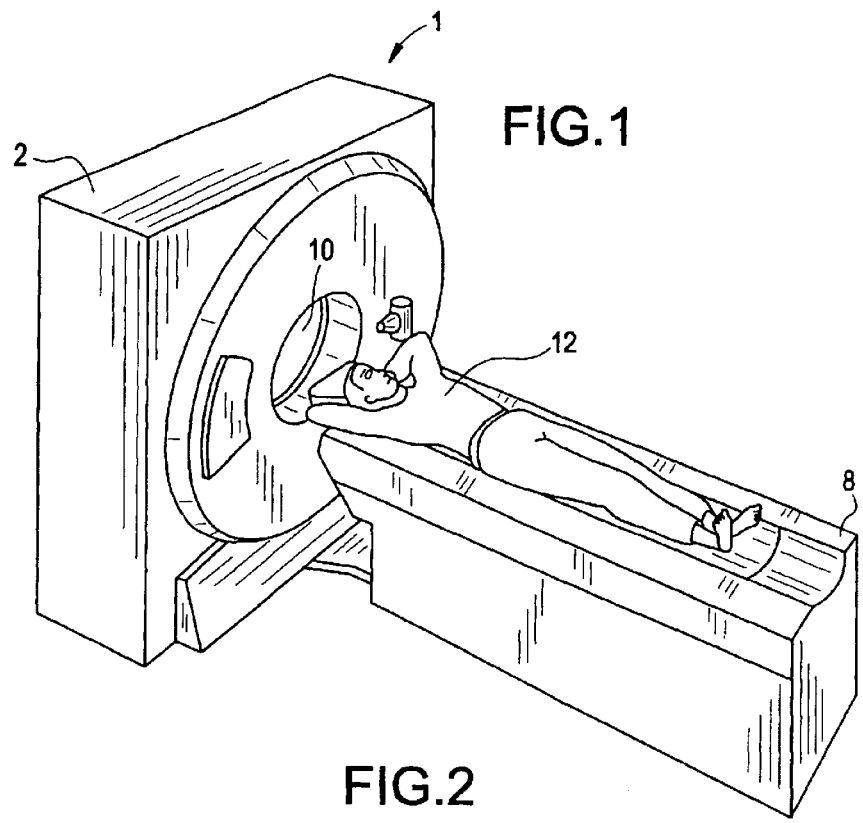
FIG. 1 is a perspective view of a CT imaging system and a patient disposed for imaging.
Figure 2:
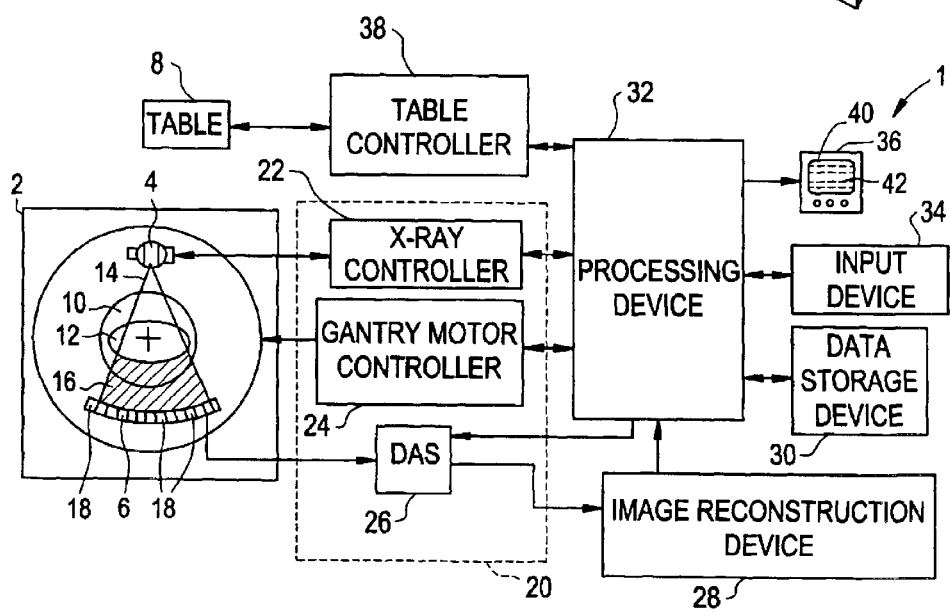
FIG. 2 is a block schematic diagram of a CT imaging system.

Referring initially to FIGS. 1 and 2 there is shown a representative CT imaging system 1 suitable for practicing the present invention embodiments. The system 1 includes a gantry 2 having an x-ray source 4, a radiation detector array 6, a patient support structure 8 and a patient cavity 10, wherein the x-ray source 4 and the radiation detector array 6 are opposingly disposed so as to be separated by the patient cavity 10. A patient 12 is shown disposed upon a patient support structure 8 which in turn is disposed within patient cavity 10. The X-ray source 4 projects an x-ray beam 14 toward radiation detector array 6 so as to pass through patient 12. The X-ray beam 14 is preferably collimated by a collimator (not shown) so as to lie within an X-Y plane of a Cartesian coordinate system referred to as an "imaging plane". After passing through and becoming attenuated by patient 12, the attenuated x-ray beam 16 is received by the radiation detector array 6. The radiation detector array 6 may include a plurality of detector elements 18, wherein each of the detector elements 18 receives an attenuated x-ray beam 16 and produces an electrical signal responsive to the intensity of attenuated x-ray beam 16.

In addition, the x-ray source 4 and radiation detector array 6 are rotatingly disposed relative to the gantry 2 and the patient support structure 8, so as to allow x-ray source 4 and radiation detector array 6 to rotate around the patient support structure 8 when it is disposed within patient cavity 10. X-ray projection data is then obtained by rotating x-ray source 4 and radiation detector array 6 around patient 10 during a scan. The rotation and operation of the X-ray source 4 and radiation detector array 6 are controlled by a control mechanism 20 associated with the CT imaging system 1.

More specifically, the control mechanism 20 includes an x-ray controller 22 in communication with x-ray source 4, a gantry motor controller 24, and a data acquisition system (DAS) 26 in communication with the radiation detector array 6. The x-ray controller 22 provides power and timing signals to x-ray source 4, gantry motor controller 24 controls the rotational speed and angular position of the x-ray source 4, while the radiation detector array 6 and DAS 26 receive the electrical signal data produced by detector elements 18, to be converted into digital signals for subsequent processing. To this end, the CT imaging system 1 also includes an image reconstruction device 28, a data storage device 30 and a processing device 32, wherein the processing device 32 further communicates with the image reconstruction device 28, the gantry motor controller 24, the x-ray controller 22 and the data storage device 30, as well as with an input device 34 and an output device 36. Finally, the CT imaging system 1 also features a table controller 38 in communication with the processing device 32 and the patient support structure 8, so as to control the position of the patient support structure 8 relative to patient cavity 10.

During the operation of the CT imaging system 1, the patient 12 is situated upon then patient support structure 8, which is then positioned by an operator (via processing device 32) within the patient cavity 10. The gantry motor controller 24 is then operated via the processing device 32, thereby causing the x-ray source 4 and the radiation detector array 6 to rotate relative to patient 12. The X-ray controller 22 is operated via processing device 32 so as to cause x-ray source 4 to emit and project a collimated x-ray beam 14 toward radiation detector array 6 and hence toward patient 12. X-ray beam 14 passes through patient 12 so as to create an attenuated x-ray beam 16, which is received by radiation detector array 6.

Upon receiving the attenuated x-ray beam 16, the detector elements 18 produce electrical signal data responsive to the intensity of the attenuated x-ray beam 16, thereafter and communicating this electrical signal data to the DAS 26. The DAS 26 then converts electrical signal data to digital signals and sends both the digital signals and the electrical signal data to the image reconstruction device 28 for high-speed image reconstruction. This image reconstruction information is then communicated to processing device 32, which stores the image in data storage device 30 and displays the digital signal as an image via output device 36.

As stated previously, it is desirable to be able to apply a minimum radiation dosage to a patient while still being able to obtain suitable image quality for diagnostic purposes. In lieu of subjecting a patient to multiple scans at varying doses, therefore, there is disclosed a method and system for simulation of a CT image at low doses. Briefly stated, a patient is scanned once in the usual manner as prescribed by existing diagnostic clinical practice standards. Then, the patient's scan data is used to create images at simulated lower doses by the introduction of noise data therewith. As will be described hereinafter, in one embodiment the noise data is combined with the raw scan data, while in another embodiment, the noise data is combined with the image data. In either case, the both the image data and associated noise data are used to reconstruct an image (simulated image data) that simulates data obtained via a lower dose scan.

Simulating patient images at lower radiation doses may be accomplished in at least two ways. One way to simulate patient images at lower radiation doses includes generating noise via a random number generator having a Poisson distribution and associating this noise with image data in order to simulate a lower dose (mA value) than that used for the scan. This advantageously allows the image data and associated noise data to be used to reconstruct an image (simulated image data) that simulates data obtained via a lower dose scan.

Referring to FIG. 3, a first embodiment of a method 100 for simulating patient images at lower radiation doses using imaging system 1 is shown and discussed. The embodiment associated with method 100 is characterized by generating noise via a random number generator having a Poisson distribution and associating this noise with image data in order to simulate a lower dose (mA value) than that used for the scan. The method 100 begins at block 102, where both the image data and noise data are obtained. The image data may be obtained via imaging system 1, wherein the image data includes image data sample elements and is responsive to patient 12. The noise data is preferably obtained via a random number generator having a Poisson distribution and preferably includes noise data sample elements. However, it will be appreciated that the noise data may also be generated using any signal generating device and/or method suitable to the desired end purpose. Once the noise data and the image data have been obtained, the amount of noise data to be added to each image data sample element may then be determined.

Because the noise sought to simulated (i.e., the quantum noise) is proportional to the inverse square root of the number of photons, the amount of noise data to be added to each image data sample element follows a Poisson distribution. Therefore, each image data sample element is the number of detected photons multiplied by a gain factor multiplier. As such, the amount of Poisson distributed noise to be associated with each image data sample element may be determined using the following equation:

$$a = \beta \sqrt{D\left(\frac{1}{\alpha} - 1\right)};$$ eq. (1)

wherein is a weighting factor applied to the Poisson distributed noise to be associated with a corresponding image data sample element, $\beta$ is a scale factor whose value depends on the DAS gain and the image processing characteristics, $\alpha$ is the mA (dose) reduction factor (value <0.1) relative to the mA of the original projection and D is the DAS signal level for the image data sample element.

Once the Poisson distributed noise for each image data sample element has been determined, the noise data is processed so as to create processed noise data, as shown in block 104. This is accomplished by multiplying the Poisson distributed noise from the random number generator for each image data sample element by the corresponding noise scale factor a, thereby creating processed noise data having processed noise data elements.

Once the processed noise data has been created, the processed noise data is then associated with the image data to create pre-image data, as shown in block 106. This is accomplished by adding the processed noise data elements with the corresponding image data sample elements. Once this has been completed, the pre-image data is then reconstructed to produce simulated image data, as shown in block 108. This simulated image data may then be displayed as an image as if it were collected using an mA tube current value of at times the mA tube current of the original patient scan.

Moreover, a may be approximated by determining the maximum value of D for each projection for which a value of $\beta$ has been predetermined to produce a constant value of to be applied to the Poisson distributed noise. In addition, although is preferably determined empirically to match fit results, $\beta$ may also be determined using any method and/or device suitable to the desired end purpose. Furthermore, non-quantum noise may also be observed in image data and may combine with the photon noise when the signal levels are low enough. One such source of non-quantum noise may be electronic noise generated via a DAS.

In the case of non-quantum noise, the Poisson distributed noise P may be multiplied by an additional scaling factor $N_n$ to account for the contribution due to non-quantum noise. If the image data signal is small enough such that the non-quantum noise is significant, the scaling factor $N_n$ should be determined so as to increase the Poisson distributed noise a such that the total added noise compensates for the quantum noise as well as the non-quantum noise in the simulated image data. In accordance with a first embodiment, the total noise associated with the image data is determined using the following equation:

$$\sigma_a = a N_n P$$ eq. (2);

wherein a is the amount of Poisson distributed noise to associated with a corresponding image data sample element as given above from equation (1), $N_n$ is the noise contribution due to non-quantum noise and P is the Poisson distributed noise from the random number generator. However, if the image data signal is large enough such that the non-quantum noise is insignificant (generally less than 10 times the amplitude of the total quantum noise), the value of $N_n$ will be equal to unity or 1.

Referring to FIG. 4, an alternative embodiment of a method 200 for simulating patient images at lower radiation doses using imaging system 1 is shown and discussed. Beginning at block 202, image data and noise data are first obtained. The image data is preferably obtained via imaging system 1, wherein the image data includes image data sample elements and is responsive to patient 12. The noise data is this instance is preferably obtained by scanning a plurality of phantom objects for each bowtie filter and kV setting of imaging system 1. As such, the noise data preferably includes a set of 10 (minimum) noise pattern images responsive to a variety of phantoms, a variety of bowtie filters, the scanning technique and a variety of emitter tube voltage levels. For example, to extract the noise data, two scans of a phantom object are performed and the obtained images are subtracted so as to obtain a raw noise pattern for each of the images. Any pixels that contain phantom edge structure after the subtraction are replaced with a random value having a standard deviation equivalent to that in the random area of the noise pattern.

Once the noise data (and thus the noise pattern images) have been obtained, they are stored in data storage device 30. These noise pattern images are preferably predetermined and include a sufficient number of individual noise pattern images so as to allow various combinations thereof to be used, thereby avoiding reusing the same combinations too frequently.

After the noise data has been obtained, the noise data is processed to create processed image noise data, as shown in block 204. This is accomplished by examining the stored noise pattern images so as to identify the noise pattern images that corresponds to a phantom shape and scan technique that best matches the physical shape of patient 12 and the scan technique employed to scan patient 12. Once the noise pattern images that best fit the patient and the scan technique have been determined, a predetermined number of selected noise pattern images are randomly selected so as to create processed noise data. Since noise adds as the square root of the sum of the squares, the noise images are scaled (i.e., multiplied) by the inverse square root of the number of noise images selected.

Finally, the processed image noise data is associated with the patient image data to create a simulated image, as shown in block 206. This may be accomplished by adding the randomly selected noise pattern images to in order obtain a resultant noise pattern image. This resultant noise pattern image is interpolated to match the DFOV of the patient image and is then scaled by a scaling factor s, wherein the scaling factor s is determined to simulate a desired low dose image. The scaling factor s may be determined through the following equation(s):

$$s = \frac{\sigma_a}{\sigma_p}; \quad \text{with}$$

$$\sigma_a = \sqrt{\sigma_f^2 - \sigma_0^2} = \sigma_0 \sqrt{\left(\frac{1}{\alpha} - 1\right)}$$

wherein, $\sigma_a$ is the standard deviation of the noise pattern to be added to the original patient image, $\sigma_p$ the standard deviation of the randomly selected interpolated and summed noise patterns, $\sigma_f$ is the standard deviation desired for the dose reduced patient image, $\sigma_o$ is the standard deviation of the original patient image and $\alpha$ is the mAs (dose) reduction factor (value<1) relative to the tube current of the original image.

Moreover, the noise value of the original image $\sigma_o$ may also be estimated by equating $\sigma_o$ with the noise pattern of the selected phantom image wherein adjustments have been made to compensate for differences between the scanning technique used to obtain the original image and the scanning technique and processing used to obtain the selected phantom image. In addition, $\sigma_o$ may be determined by summing the pixel data in the vertical and horizontal orientations and subsequently using a noise prediction strategy as described in U.S. application Ser. No. 10/064,874, U.S. Pat. Publication No. 2004-0032928A1.

As will be appreciated, the above described embodiments advantageously allows for medical patients to be scanned only once in the usual manner as prescribed by current diagnostic clinical practice. Thus, patients do not receive any additional radiation exposure for research beyond what they would have received for a typical clinical diagnostic prescription. Because the patient's data (raw data and/or image data) may also be used to generate images at a simulated lower doses, researchers are able to study whether the patient dose exposure has any impact on the diagnostic outcome of the patient. As a result, patients do not have to be scanned multiple times at different doses for such clinical research.

As will also be appreciated, the disclosed simulation techniques may generally be applied in conjunction with any imaging system suitable to a desired diagnostic purpose, such as magnetic resonance imaging (MRI), ultrasound, X-Ray, CT and/or PET. In addition, the method embodiments of FIG. 3 and/or FIG. 4 may be implemented through processing device 32 operating in response to a computer program. In order to perform the prescribed functions and desired processing, as well as the computations therefore (e.g., the execution of Fourier analysis algorithm(s), the control processes prescribed herein, and the like), the controller may include, but not be limited to, a processor(s), computer(s), memory, storage, register(s), timing, interrupt (s), communication interfaces, and input/output signal interfaces, as well as combinations comprising at least one of the foregoing. For example, the controller may include signal input signal filtering to enable accurate sampling and conversion or acquisitions of such signals from communications interfaces. It is further contemplated that the embodiments that the of FIG. 3 and/or FIG. 4 may be implemented via a controller located remotely from processing device 32.

As described above, the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) can be updated to implement the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method for generating a simulated patient image, the method comprising:
   obtaining image data from an actual patient image;
   generating simulated noise data through a random number generator in accordance with a Poisson distribution;
   combining scan data from said actual patient image with said generated simulated noise data to create pre-image data;
   reconstructing said pre-image data to create simulated image data; and
   combining said simulated image data with said simulated noise data to create the simulated patient image;
   wherein individual scan data samples from said scan data are each combined with a random noise value generated from said Poisson distribution random number generator, said random noise value first being multiplied by a weighting factor to produce a weighted random noise value;
   said weighting factor determined in accordance with the equation:

$$a = \beta \sqrt{D\left(\frac{1}{\alpha} - 1\right)};$$

wherein a is said weighting factor, β is a scale factor whose value depends on a data acquisition system (DAS) gain and the image processing characteristics, α is a tube current reduction factor relative to a tube current at which said actual patient image was taken, and D is a DAS signal level for a corresponding individual scan data sample.

2. The method of claim 1, wherein, in addition to said weighting factor, each of said random noise values are further multiplied by an electronic noise scale factor prior to being combined with individual scan data samples, said electronic noise scale factor being determined in accordance with the equation:

$$\sigma_a = a N_n P;$$

wherein $N_n$ is said electronic noise scale factor due to non-quantum noise, a is said weighting factor, P is said random noise value generated from said Poisson distribution random number generator, and $\sigma_a$ is a standard deviation of said generated simulated noise data to be combined with said actual patient image.

3. A method for generating a simulated patient image, the method comprising:
obtaining image data from an actual patient image;
generating simulated noise data by creating a set of individual noise pattern images for each of a plurality of phantom objects;
selecting at least one of said individual noise pattern images to be combined with said actual patient image; and
combining said at least one selected individual noise pattern image with said actual patient image, thereby creating the simulated patient image.

4. The method of claim 3, wherein said selecting at least one of said individual noise pattern images is based upon a patient shape and an imaging technique.

5. The method of claim 3, wherein said at least one of said individual noise pattern images is randomly selected.

6. The method of claim 5, wherein if more than one of said individual noise pattern images is selected, then said noise pattern images are added together to produce a resultant noise pattern.

7. The method of claim 6, wherein said combined noise pattern is scaled by a scaling factor, s, in accordance with the equation:

$$s = \frac{\sigma_a}{\sigma_p}; \quad \text{with}$$

$$\sigma_a = \sqrt{\sigma_f^2 - \sigma_0^2} = \sigma_0 \sqrt{\left(\frac{1}{\alpha} - 1\right)}$$

wherein, $\sigma_n$ is a standard deviation of said generated simulated noise data to be combined with said actual patient image, $\sigma_p$ is a standard deviation of randomly selected interpolated and summed noise pattern images, $\sigma_f$ is a desired standard deviation desired for the simulated patient image, $\sigma_o$ is a standard deviation of said actual patient image and $\alpha$ is a tube current reduction factor relative to a tube current at which said actual patient image was taken.

8. The method of claim 7, wherein said noise pattern images are scaled by the inverse square root of the number of said noise pattern images selected.

9. A method for generating a simulated computer tomography (CT) patient image, the method comprising:
obtaining image data from an actual CT patient image taken at a first radiation dose;
generating simulated noise data; and
combining said image data with said simulated noise data to create the simulated patient image;
wherein the simulated image simulates said actual CT patient image taken at a second, reduced radiation dose with respect to said first radiation dose.

10. The method of claim 9, further comprising:
combining scan data from said actual patient image with said generated simulated noise data to create pre-image data; and
reconstructing said pro-image data to create simulated image data.

11. The method of claim 10 wherein said simulated noise data is generated through a random number generator in accordance with a Poisson distribution.

12. The method of claim 11, wherein individual scan data samples from said scan data are each combined with a random noise value generated from said Poisson distribution random number generator, said random noise value first being multiplied by a weighting factor to produce a weighted random noise value.

13. The method of claim 12, wherein said weighting factor is determined in accordance with the equation:

$$a = \beta \sqrt{D\left(\frac{1}{\alpha} - 1\right)};$$

wherein a is said weighting factor, β is a scale factor whose value depends on a data acquisition system (DAS) gain and the image processing characteristics, α is a tube current reduction factor relative to a tube current corresponding to said first radiation dose, and D is a DAS signal level for a corresponding individual scan data sample.

14. The method of claim 13, wherein, in addition to said weighting factor, each of said random noise values are further multiplied by an electronic noise scale factor prior to being combined with individual scan data samples, said electronic noise scale factor being determined in accordance with the equation:

$$\sigma_a = a N_n P;$$

wherein $N_n$ is said electronic noise scale factor due to non-quantum noise, a is said weighting factor, P is said random noise value generated from said Poisson distribution random number generator, and $\sigma_o$ is a standard deviation of said generated simulated noise data to be combined with said actual patient image.

15. The method of claim 9, further comprising:
creating a set of individual noise pattern images for each a plurality of phantom objects;
selecting at least one or said individual noise pattern images to be combined with said actual patient image; and
combining said at least one selected individual noise pattern image with said actual patient image, thereby creating the simulated patient image.

16. The method of claim 15, wherein said selecting at least one said individual noise pattern images is based upon a patient shape and an imaging technique.

17. The method of claim 16, wherein said at least one of said individual noise pattern images is randomly selected.

18. The method of claim 17, wherein if more than one of said individual noise pattern images is selected, then said noise pattern images are added together to produce a resultant noise pattern.

19. The method of claim 18, wherein said combined noise pattern is scaled by a scaling factor, s, in accordance with the equation:

$$s = \frac{\sigma_a}{\sigma_p}; \quad \text{with}$$

$$\sigma_a = \sqrt{\sigma_f^2 - \sigma_0^2} = \sigma_0 \sqrt{\left(\frac{1}{\alpha} - 1\right)}$$

wherein, $\sigma_n$ is a standard deviation of said generated simulated noise data to be combined with snid actual patient image, $\sigma_p$ is a standard deviation of randomly selected interpolated and summed noise pattern images, $\sigma_f$ is a desired standard deviation desired for the simulated patient image, $\sigma_o$ is a standard deviation of said actual patient image and $\alpha$ is a tube current reduction factor relative to a tube current corresponding to said first radiation dose.

20. The method of claim 19, wherein said noise pattern images are scaled by the inverse square root of the number of said noise pattern images selected.

21. An imaging system, comprising:
a gantry having an x-ray source and a radiation detector array, wherein said gantry defines a patient cavity and wherein said x-ray source and said radiation detector array are rotatingly associated with said gantry so as to be separated by said patient cavity;
a patient support structure moving associated with said gantry so as to allow communication with said patient cavity; and
a processing for device for obtaining image data from an actual patient image;
means for generating simulated noise data through random number generator in accordance with a Poisson distribution;
means for combining said image data with said simulated noise data to create a simulated patient image;
means for combining scan data from said actual patient image with said generated simulated noise data to create pre-image data; and
means for reconstructing said pre-image data to create simulated image data;
wherein individual scan data samples from said scan data are each combined with random noise value generated from said Poisson distribution random number generator, said random noise value first being multiplied by a weighting factor to produce a weighted random noise value;
said weighting factor determined in accordance with the equation:

$$a = \beta \sqrt{D\left(\frac{1}{\alpha} - 1\right)};$$

wherein a is said weighting factor, β is a scale factor whose value depends on a data acquisition system (DAS) gain and the image processing characteristics, α is a tube current reduction factor relative to a tube current at which said actual patient image was taken, and D is a DAS signal level for a corresponding individual scan data sample.

22. The imaging system of claim 21, wherein, in addition to said weighting factor, each of said random noise values are further multiplied by an electronic noise scale factor prior to being combined with individual scan data samples, said electronic noise scale factor being determined in accordance with the equation:

$$\sigma_a = a N_n P;$$

wherein $N_n$ is said electronic noise scale factor due to non-quantum noise, a is said weighting factor, P is said random noise value generated from said Poisson distribution random number generator, and $\sigma_o$ is a standard deviation of said generated simulated noise data to be combined with said actual patient image.

23. An imaging system, comprising:
a gantry having an x-ray source and a radiation detector array, wherein said gantry defines a patient cavity and wherein said x-ray source and said radiation detector array are rotatingly associated with said gantry so as to be separated by said patient cavity;
a patient support structure moving associated with said gantry so as to allow communication with patient cavity; and
a processing device for obtaining image data from an actual patient image;
means generating simulated noise data by
means for creating a set of individual noise pattern images for each of a plurality of phantom objects;
means for selecting at least one of said individual noise pattern images to be combined with said actual patient image; and
means for combining said at least one selected individual noise pattern image with said actual patient image, thereby creating the simulated patient image.

24. The imaging system of claim 23, wherein said means for selecting at least one of said individual noise pattern images is based upon a patient shape and an imaging technique.

25. The imaging system of claim 23, wherein said at least one of said individual noise pattern images is randomly selected.

26. The imaging system of claim 25, wherein if more than one of said individual noise pattern images is selected, then said noise pattern images are added together to produce a resultant noise pattern.

27. The imaging system of claim 26, wherein said combined noise pattern is scaled by a scaling factor, s, in accordance with the equation:

$$s = \frac{\sigma_a}{\sigma_p}; \quad \text{with}$$

$$\sigma_a = \sqrt{\sigma_f^2 - \sigma_0^2} = \sigma_0 \sqrt{\left(\frac{1}{\alpha} - 1\right)}$$

wherein, $\sigma_a$ is a standard deviation of said generated, simulated noise data to be combined with said actual patient image, $\sigma_p$ is a standard deviation of randomly selected interpolated and summed noise pattern images, $\sigma_l$ is a desired standard deviation desired for the simulated patient image, $\sigma_o$ is a standard deviation of said actual patient image and α is a tube current reduction factor relative to a tube current at which said actual patient image was taken.

28. The imaging system of claim 27, wherein said noise pattern images are scaled by the inverse square root of the number of said noise pattern images selected.

29. A storage medium, comprising:
a machine readable computer program code for generating a simulated patient image; and
instructions for causing a computer to implement a method, the method further comprising;
   obtaining image data from an actual patient image;
   generating simulated noise data through a random number generator in accordance with a Poisson distribution;
   combining scan data from said actual patient image with said generated simulated noise data to create pre-image data;
   reconstructing said pre-image data to create simulate image data; and
   combining said simulated image data with said simulated noise data to create the simulated patient image;
wherein individual scan data samples from said scan data are each combined with random noise value generated from said Poisson distribution random number generator, said random noise value first being multiplied by a weighting factor to produce a weighted random noise value;
said weighting factor is determined in accordance with the equation:

$$a = \beta\sqrt{D\left(\frac{1}{\alpha} - 1\right)};$$

wherein a is said weighting factor, $\beta$ is a scale factor whose value depends on a data acquisition system (DAS) gain and the image processing characteristic, $\alpha$ is a tube current reduction factor relative to a tube current at which said actual patient image was taken, and D is a DAS signal level for a corresponding individual scan data sample.

30. The storage medium of claim 29, wherein, in addition to said weighting factor, each of said random noise values are further multiplied by an electronic noise scale factor prior to being combined with individual scan data samples, said electronic noise scale factor being determined in accordance with the equation:

$$\sigma_a = aN_rP;$$

wherein $N_A$ is said electronic noise scale factor due to non-quantum noise, a is said weighting factor, P is said random noise value generated from said Poisson distribution random number generator, and $\sigma_o$ is a standard deviation of said generated simulated noise data to be combined with said actual patient image.

31. A storage medium, comprising:
a machine readable computer program code for generating a simulated patient image; and
instructions for causing a computer to implement a method, the method further comprising;
   obtaining image data from an actual patient image;
   generating simulated noise data by creating a set of individual noise pattern images for each of a plurality of phantom objects;
   selecting at least one of said individual noise pattern images to be combined with said actual patient image; and
   combining said at least one selected individual noise pattern image with said actual patient image, thereby creating the simulated patient image.

32. The storage medium of claim 31, wherein said selecting at least one of said individual noise pattern images is based upon a patient shape and an imaging technique.

33. The storage medium of claim 31, wherein said at least one of said individual noise pattern images is randomly selected.

34. The storage medium of claim 33, wherein if more than one of said individual noise pattern images is selected, then said noise pattern images are added together to produce a resultant noise pattern.

35. The storage medium of claim 34, wherein said combined noise pattern is sealed by a scaling factor, s, in accordance with the equation:

$$s = \frac{\sigma_a}{\sigma_p}; \quad \text{with}$$

$$\sigma_a = \sqrt{\sigma_f^2 - \sigma_0^2} = \sigma_0\sqrt{\left(\frac{1}{\alpha} - 1\right)}$$

wherein, $\sigma_a$ is a standard deviation of said generated simulated noise data to be combined with said actual patient image, $\sigma_p$ is a standard deviation of randomly selected interpolated and summed noise pattern images, $\sigma_f$ is a desired standard deviation desired for the simulated patient image, $\sigma_o$ is a standard deviation of said actual patient image and $\alpha$ is a tube current reduction factor relative to a tube current at which said actual patient image was taken.

36. The storage medium of claim 35, wherein said noise pattern images are scaled by the inverse square root of the number of said noise pattern images selected.

37. A computer data signal, comprising:
code configured to cause a processor to implement a method for generating a simulated patient image, the method further comprising;
   obtaining image data from an actual patient image;
   generating simulated noise data through a random number generator in accordance with a Poisson distribution;
   combining scan data from said actual patient image with said generated simulated noise data to create pre-image data;
   reconstructing said pre-image data to create simulated image data; and
   combining said simulated image data with said simulated noise, data to create the simulated patient image;
wherein individual scan data samples from said scan data are each combined with a random noise value generated from said Poisson distribution random number generator, said random noise value first being multiplied by a weighting factor to produce a weighed random value;
said weighting factor determined in accordance with the equation:

$$a = \beta\sqrt{D\left(\frac{1}{\alpha} - 1\right)};$$

wherein a is said weighting factor, $\beta$ is a scale factor whose value depends on a data acquisition system (DAS) gain and the image processing characteristics, $\alpha$ is a tube current reduction factor relative to a tube current at which said actual patient image was taken, and D is a DAS signal level for a corresponding individual scan data sample.

38. The computer data signal of claim 37, wherein, in addition to said weighting factor, each of said random noise values are further multiplied by an electronic noise scale factor prior to being combined with individual scan data samples, said electronic noise scale factor being determined in accordance with the equation:

$$\sigma hd\ a = aN_n P$$

wherein $N_n$ is said electronic noise scale factor due to non-quantum noise, a is said weighting factor, P is said random noise value generated from said Poisson distribution random number generator, and $\sigma_a$ is a standard deviation of said generated simulated noise data to be combined with said actual patient image.

39. A computer data signal comprising:
code configured to cause a processor to implement a method for generating a simulated patient image, the method further comprising:
obtaining image data from an actual patient image;
generating simulated noise data by creating a set of individual noise pattern images for each a plurality a phantom objects;
selecting at least one of said individual noise pattern images to be combined with said actual patient image; and
combining said at least one selected individual noise pattern image with said actual patient image, thereby creating the simulated patient image.

40. The computer data signal of claim 39, wherein said selecting at least one of said individual noise pattern images is based upon a patient shape and an imaging technique.

41. The computer data signal of claim 39, wherein said selecting at least one of said individual noise pattern images is based upon a patient shape and an imaging technique.

42. The computer data signal of claim 41, wherein if more than one of said individual noise pattern images is selected, then said noise pattern images are added together to produce a resultant noise pattern.

43. The computer data signal of claim 42, wherein said combined noise pattern is scaled by a scaling factor, s, in accordance with the equation:

$$s = \frac{\sigma_a}{\sigma_p}; \quad \text{with}$$

$$\sigma_a = \sqrt{\sigma_f^2 - \sigma_o^2} = \sigma_o \sqrt{\left(\frac{1}{\alpha} - 1\right)}$$

wherein, $\sigma_a$ is a standard deviation of said generated simulated noise data to be combined with said actual patient image, $\sigma_p$ is a standard deviation of randomly selected interpolated and summed noise pattern images, $\sigma_f$ is a desired standard deviation desired for the simulated patient image, $\sigma_o$ is a standard deviation of said actual patient image and $\alpha$ is a tube current reduction factor relative to a tube current at which said actual patient image was taken.

44. The computer data signal of claim 43, wherein said noise pattern images are scaled by the inverse square root of the number of said noise pattern images selected.

* * * * *

UNITED STATES PATENT AND TRADEMARK OFFICE
CERTIFICATE OF CORRECTION

PATENT NO.        : 6,829,323 B2
APPLICATION NO.   : 10/064586
DATED             : December 7, 2004
INVENTOR(S)       : Toth et al.

It is certified that error appears in the above-identified patent and that said Letters Patent is hereby corrected as shown below:

Column 5:
Line 19, after "to" delete "simulated" and insert therefor -- simulate --
Line 32, after "wherein" insert -- $a$ --
Line 45, after "factor" delete "a" and insert therefor -- $a$ --
Line 59, after "Moreover," delete "a" and insert therefor -- $a$ --
Column 6:
Line 6, after "noise" delete "a" and insert therefor -- $a$ --
Line 14, after "wherein" delete "a" and insert therefor -- $a$ --
Column 8:
Line 65, after "wherein" delete "a" and insert therefor -- $a$ --
Column 9:
Line 15, after "noise," delete "a" and insert therefor -- $a$ --
Line 52, after "wherein," delete "$\sigma_n$" and insert therefor -- $\sigma_a$ --
Column 10:
Line 11, after "said" delete "pro-image" and insert therefor -- pre-image --
Line 49, after "and" delete "$\sigma_o$" and insert therefor -- $\sigma_a$ --
Column 11:
Line 13, after "wherein," delete "$\sigma_n$" and insert therefor -- $\sigma_a$ --
Column 12:
Line 20, after "structure" delete "moving" and insert therefor -- movingly --
Line 21, after "with" insert therefor -- said --
Line 25, after "means" insert therefor -- for --
Line 26, before "creating" delete "means for"
Line 60, before "is a" delete "$\sigma_1$" and insert therefor -- $\sigma_{f''}$ --

UNITED STATES PATENT AND TRADEMARK OFFICE
CERTIFICATE OF CORRECTION

PATENT NO. : 6,829,323 B2
APPLICATION NO. : 10/064586
DATED : December 7, 2004
INVENTOR(S) : Toth et al.

It is certified that error appears in the above-identified patent and that said Letters Patent is hereby corrected as shown below:

Column 13:
Line 13, after ":create" delete "simulate" and insert therefor -- simulated --
Line 19, after "with" insert therefor -- $a$ --
Line 24, after "factor" delete "is"
Line 31, after "wherein" delete "a" and insert therefor -- $a$ --
Line 47, after "wherein" delete "$N_A$" and insert therefor -- $N_n$ --
Line 48, after "noise" delete "a" and insert therefor -- $a$ --
Line 50, after "and" delete "$\sigma_o$" and insert therefor -- $\sigma_a$ --
Column 14:
Line 47, after "noise" delete ","
Line 63, after "wherein" delete "a" and insert therefor -- $a$ --
Column 15:
Line 10, after "equation:" delete "σ hd a " and insert therefor -- $\sigma_a$ --
Line 13, after "noiser," delete "a" and insert therefor -- $a$ --

Signed and Sealed this

Third Day of October, 2006

JON W. DUDAS
*Director of the United States Patent and Trademark Office*